US006147231A

United States Patent [19]

Takase et al.

[11] Patent Number: 6,147,231

[45] Date of Patent: Nov. 14, 2000

[54] PROCESS FOR PRODUCING 2(2-HYDROXYMETHYLPHENYL)ACETAMIDE DERIVATIVE AND INTERMEDIATE FOR THE PRODUCTION THEREOF

[75] Inventors: Akira Takase, Otsu; Hiroyuki Kai, Yamatokoriyama; Takami Murashi, Shiga, all of Japan

[73] Assignee: Shionogi & Co., Ltd., Osaka, Japan

[21] Appl. No.: 09/174,256

[22] Filed: Oct. 16, 1998

Related U.S. Application Data

[62] Division of application No. 08/849,218, filed as application No. PCT/JP95/02621, Dec. 21, 1995, Pat. No. 5,856,573.

[30] Foreign Application Priority Data

Dec. 26, 1994 [JP] Japan .................................... 6-322130

[51] Int. Cl.[7] .................................................. C07D 315/00

[52] U.S. Cl. .............................. 549/420; 549/28; 549/62; 549/465; 549/475; 556/465; 562/840; 562/843

[58] Field of Search .................................... 562/840, 843; 549/28, 62, 420, 475; 556/465

[56] References Cited

U.S. PATENT DOCUMENTS

| | | | |
|---|---|---|---|
| 5,387,714 | 2/1995 | Takase et al. | 562/843 |
| 5,414,122 | 5/1995 | Murabayashi et al. | 564/129 |

FOREIGN PATENT DOCUMENTS

| | | |
|---|---|---|
| 477 631 | 4/1992 | European Pat. Off. . |
| 535 928 | 4/1993 | European Pat. Off. . |
| 617 011 | 9/1994 | European Pat. Off. . |

*Primary Examiner*—Shailendra Kumar
*Attorney, Agent, or Firm*—Foley & Lardner

[57] ABSTRACT

A process for producing a compound of the formula (I):

(I)

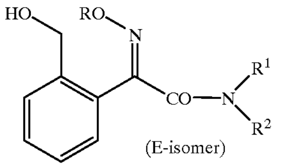

wherein $R^1$ and $R^2$ are the same or different and are hydrogen or alkyl, and R is hydrogen or alkyl, which comprises removing the protective group (P) of hydroxyl of a compound of the formula (II):

(II)

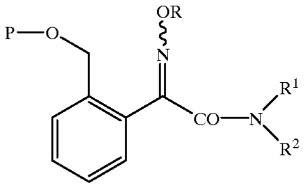

wherein P is a protective group of hydroxyl, ~ indicates an E-isomer, Z-isomer or a mixture thereof, and the other symbols are as defined above; and an intermediate for the production of the compound of the formula (I).

4 Claims, No Drawings

PROCESS FOR PRODUCING 2(2-HYDROXYMETHYLPHENYL)ACETAMIDE DERIVATIVE AND INTERMEDIATE FOR THE PRODUCTION THEREOF

This application is a divisional of application Ser. No. 08/084,218, filed Jun. 10, 1997, now U.S. Pat. No. 5,856,573 which is a national stage of PCT/JP95/02621 filed Dec. 21, 1995.

FIELD OF THE INVENTION

The present invention relates to a process for producing a 2-(2-hydroxymethylphenyl)acetamide derivative, particularly a 2-(2-hydroxymethylphenyl)-2-alkoxy(or hydroxy) iminoacetamide, which is an intermediate for the production of alkoxyiminoacetamide compounds useful as agricultural fungicides. The present invention also relates to an intermediate for the production of the 2-(2-hydroxymethylphenyl) acetamide derivative.

BACKGROUND OF THE INVENTION

A 2-(2-hydroxymethylphenyl)-2-alkoxy(or hydroxy) iminoacetamide is an important intermediate for the production of alkoxyiminoacetamide derivatives useful as agricultural fungicides (see JP-A 3-246268, JP-A 4-182461). The following processes for producing the intermediate are known: the process comprising reacting a 2-(2-halomethylphenyl)-2-alkoxyiminoacetic acid ester with a metal acetate, followed by an amine (JP-A 3-246268), and the process comprising converting the halomethyl group of a 2-(2-halomethylphenyl)-2-alkoxyiminoacetamide to a hydroxymethyl group (JP-A 5-097768).

However, there is still room for improvement in these processes.

The object of the present invention is to provide an industrially advantageous process for producing a 2-(2-hydroxymethylphenyl)-2-alkoxy(or hydroxy) iminoacetamide.

Another object of the present invention is to provide an intermediate for the production of a 2-(2-hydroxymethylphenyl)-2-alkoxy(or hydroxy) iminoacetamide.

DISCLOSURE OF THE INVENTION

The present inventors have intensively researched to achieve the above objects. As a result, it has been found that a 2-(2-hydroxymethylphenyl)-2-alkoxy(or hydroxy) iminoacetamide can be obtained by subjecting the corresponding compound in which the hydroxyl group of the hydroxymethyl group is protected to deprotection. Thus, the present invention has been accomplished.

The present invention relates to a process for producing a compound of the formula (I):

(I)

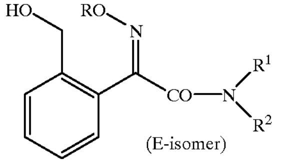

(E-isomer)

wherein $R^1$ and $R^2$ are the same or different and are hydrogen or alkyl, and R is hydrogen or alkyl, which comprises removing the protective group (P) of hydroxyl of a compound of the formula (II):

(II)

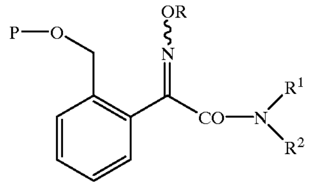

wherein P is a protective group of hydroxyl, ~ indicates an E-isomer, Z-isomer or a mixture thereof, and the other symbols are as defined above.

In a preferred aspect, the present invention relates to a process for producing a compound of the formula (I-2):

(I-2)

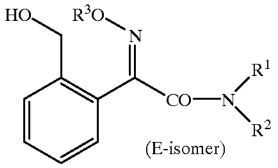

(E-isomer)

wherein $R^3$ is alkyl and the other symbols are as defined above, which comprises removing a protective group (P) of hydroxyl of a compound of the formula (II-1):

(II-1)

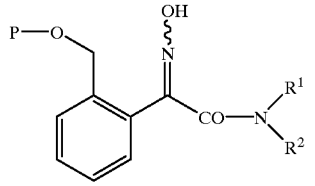

wherein each symbol is as defined above, to obtain a compound of the formula (I-1):

(I-1)

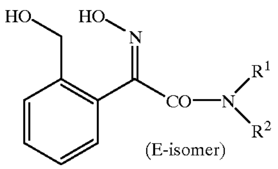

(E-isomer)

wherein each symbol is as defined above, and then alkylating the compound of the formula (I-1).

In the present invention, the compound of the formula (II) can be obtained by reacting a compound of the formula (IV):

(IV)

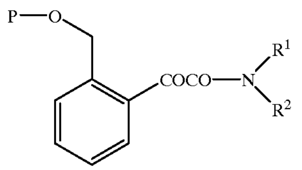

wherein each symbol is as defined above, with a compound of the formula (III):

$NH_2OR$ (III)

wherein R is as defined above.

The present invention also provides a compound of the formula (II'):

(II')

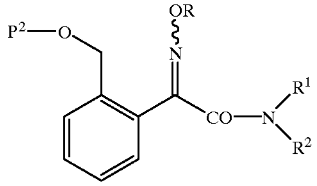

wherein $R^1$ and $R^2$ are the same or different and are hydrogen or alkyl, R is hydrogen or alkyl, $P^2$ is aralkyl, trialkylsilyl, triaralkylsilyl, alkyldiarylsilyl, alkoxyalkyl, alkoxyalkoxyalkyl, alkylthioalkyl, tetrahydropyranyl, tetrahydrothiopyranyl, tetrahydrofuranyl, tetrahydrothiofuranyl or aralkyloxyalkyl, and ~ indicates an E-isomer, Z-isomer or a mixture thereof; and a compound of the formula (IV'):

(IV')

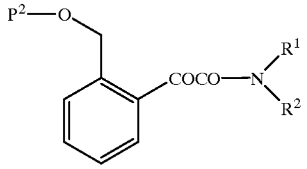

wherein each symbol is as defined above (The compounds of the formulas (II') and (IV') are included in the above formulas (II) and (IV), respectively).

The alkyl represented by R, $R^1$, $R^2$ and $R^3$ in the above formulas includes, for example, alkyl having 1 to 8 carbon atoms, preferably 1 to 6 carbon atoms, such as methyl, ethyl, propyl, isobutyl, sec-butyl, t-butyl, etc. In particular, methyl is preferred.

The protective groups of hydroxyl represented by P and $P^2$ include, for example, conventional protective groups of a hydroxyl group, such as ether-type protective groups, acetal-type protective groups, etc., described in T. W. Green, “Protective Groups in Organic Synthesis”, p. 1–113, John Willy & Sons (1981); C. B. Reese, “Protective Groups in Organic Chemistry”, edited by J. F. McOmie, p. 95–143, Plenum Press (1973), etc.

The ether-type protective groups include, for example, alkyl (e.g., $C_{1-6}$ alkyl, preferably $C_{1-4}$ alkyl, such as methyl, ethyl, propyl, t-butyl, etc.), alkenyl (e.g., $C_{2-6}$ alkenyl, preferably $C_{2-4}$ alkenyl, such as allyl, etc.), aralkyl (e.g., substituted or unsubstituted $C_{6-10}$ aryl-$C_{1-4}$ alkyl, such as benzyl, p-methoxybenzyl, triphenylmethyl, etc.), trialkylsilyl (e.g., tri($C_{1-6}$ alkyl)silyl such as triisopropylsilyl, t-butyldimethylsilyl, etc.), alkyldiarylsilyl (e.g., ($C_{1-6}$ alkyl) di($C_{6-10}$ aryl)silyl such as t-butyldiphenylsilyl, etc.), triaralkylsilyl groups (e.g., tribenzylsilyl, etc.), etc.

The acetal-type protective groups include, for example, alkoxyalkyl (e.g., $C_{1-4}$ alkoxy-$C_{1-4}$ alkyl such as methoxymethyl, 1-ethoxyethyl, 1-methyl-1-methoxyethyl, etc.), alkoxyalkoxyalkyl (e.g., $C_{1-4}$ alkoxy-$C_{1-4}$ alkoxy-$C_{1-4}$ alkyl such as methoxyethoxymethyl, etc.), alkylthioalkyl (e.g., $C_{1-4}$ alkylthio-$C_{1-4}$ alkyl such as methylthiomethyl, etc.), tetrahydropyranyl (e.g., tetrahydropyran-2-yl, 4-methoxytetrahydropyran-4-yl, etc.), tetrahydrothiopyranyl (e.g., tetrahydrothiopyran-2-yl, etc.), tetrahydrofuranyl (e.g., tetrahydrofuran-2-yl, etc.), tetrahydrothiofuranyl (e.g., tetrahydrothiofuran-2-yl, etc.), aralkyloxyalkyl (e.g., benzyloxymethyl, etc.), etc.

Preferably, the protective groups are removable by acid treatment, particularly removable by acid treatment and stable under conditions for the synthesis of a Grignard reagent (e.g., the compound (VIII) described below) or basic conditions. Preferred examples of the protective groups include aralkyl (e.g., triphenylmethyl, etc.), trialkylsilyl (e.g., t-butyldimethylsilyl, triisopropylsilyl, etc.), triaralkylsilyl (e.g., tribenzylsilyl, etc.), alkoxyalkyl (e.g., methoxymethyl, 1-ethoxyethyl, 1-methyl-1-methoxyethyl, etc.), tetrahydropyranyl (e.g., tetrahydropyran-2-yl, etc.), tetrahydrothiopyranyl (e.g., tetrahydrothiopyran-2-yl, etc.), tetrahydrofuranyl (e.g., tetrahydrofuran-2-yl, etc.), tetrahydrothiofuranyl (e.g., tetrahydrothiofuran-2-yl, etc.), etc. In particular, tetrahydropyran-2-yl, 1-ethoxyethyl and tetrahydrofuran-2-yl are preferred.

The compounds of the formulas (II) and (II-1) and (II-2) described below exist as E- or Z-isomers. These compounds include E- or Z-isomers and mixtures thereof unless otherwise indicated. In the above formulas, this is indicated by the wave line ~.

The compounds of the formulas (I), (I-1), (I-2) and (II-1) may be in salt forms. Examples of the salts include alkaline metal salts (e.g., sodium salts, potassium salts, lithium salts, etc.), etc.

Preferred examples of the compound of the formula (I) include the compound of the formula (I) wherein R is a hydrogen atom or methyl, and $R^1$ and $R^2$ are a hydrogen atom; and the compound of the formula (I) wherein R is a hydrogen atom or methyl, and any one of $R^1$ and $R^2$ is a hydrogen atom and the other is methyl.

Preferred embodiments of the process of the present invention are as follows.

The desired compound of the formula (I) (hereinafter sometimes abbreviated to the compound (I); the other compounds are also abbreviated in the same manner) consists of the compound (I-1) wherein R is a hydrogen atom and the compound (1-2) wherein R is alkyl. The compound (I-1) can be prepared according to Scheme 1, and the compound (I-2) can be prepared according to Scheme 3 or 4.

Scheme 1

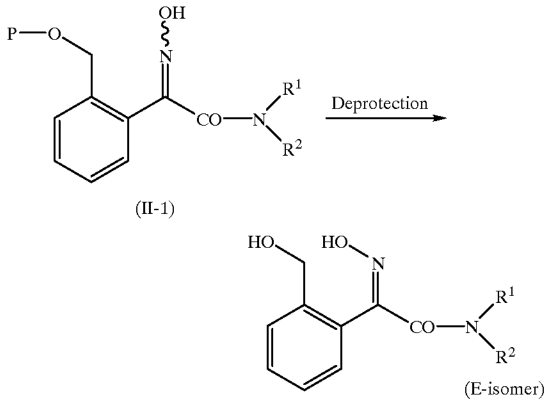

(II-1)

(I-1)

(E-isomer)

wherein each symbol is as defined above.

That is, the compound (I-1) can be obtained by removing the protective group (P) of hydroxyl of the compound (II-1).

In this reaction, the protective group of hydroxyl is removed and the isomerization to the E-isomer proceeds at the same time. Therefore, a separate isomerization step to the E-isomer is not required, and the compound (I-1) can be obtained in high yield and purity.

This reaction can be carried out by conventional deprotection methods of protected hydroxyl, for example, by those described in T. W. Green, "Protective Groups in Organic Synthesis", p. 1–113, John Willy & Sons (1981); C. B. Reese, "Protective Groups in Organic Chemistry", edited by J. F. McOmie, p. 95–143, Plenum Press (1973), etc.

For example, when the protective group of hydroxyl is alkyl (e.g., t-butyl, etc.), alkenyl (e.g., allyl, etc.), aralkyl (e.g., triphenylmethyl, etc.), trialkylsilyl (e.g., t-butyldimethylsilyl, triisopropylsilyl, etc.), alkyldiarylsilyl (e.g., t-butyldiphenylsilyl, etc.), triaralkylsilyl (e.g., tribenzylsilyl, etc.), alkoxyalkyl (e.g., methoxymethyl, 1-ethoxyethyl, 1-methyl-1-methoxyethyl, etc.), alkoxyalkoxyalkyl (e.g., methoxyethoxymethyl, etc.), alkylthioalkyl (e.g., methylthiomethyl, etc.), tetrahydropyranyl (e.g., tetrahydropyran-2-yl, 4-methoxytetrahydropyran-4-yl, etc.), tetrahydrothiopyranyl (e.g., tetrahydrothiopyran-2-yl, etc.), tetrahydrofuranyl (e.g., tetrahydrofuran-2-yl, etc.), tetrahydrothiofuranyl (e.g., tetrahydrothiofuran-2-yl, etc.), or aralkyloxyalkyl (e.g., benzyloxymethyl, etc.), the deprotection can be carried out by treating the compound (II-1) with an acid.

The acids that can generally be used include, for example, inorganic acids such as hydrohalogenic acids (e.g., hydrochloric acid, hydrobromic acid, hydroiodic acid, etc.), hydrogen halides (e.g., hydrogen chloride, hydrogen bromide, hydrogen iodide, etc.), boric acid, phosphoric acid, sulfuric acid, etc.; sulfonic acids (e.g., aliphatic sulfonic acids such as trifluoromethanesulfonic acid and aromatic sulfonic acids such as toluenesulfonic acid, etc.), carboxylic acids (e.g., acetic acid, trifluoroacetic acid, etc.), silica gel, Lewis acids [e.g., aluminium halides (e.g., aluminium chloride, etc.), zinc chloride, titanium tetrachloride, etc.]. One or more appropriate acids can be selected from these acids.

The amount of the acid to be used is a trace amount to 1 equivalent. Alternatively, carboxylic acids can be used as solvents.

The solvents to be used include, for example, hydrocarbons (e.g., benzene, toluene, xylene, etc.), halogenated hydrocarbons (e.g., dichloromethane, 1,2-dichloroethane, etc.), ethers (e.g., tetrahydrofuran, dioxane, etc.), alcohols (e.g., methanol, ethanol, etc.), nitriles (e.g., acetonitrile, etc.), water, etc., and mixed solvent thereof. The reaction temperature is −80 to 150° C., preferably −10 to 80° C. The reaction time is 1 minute to 3 hours, preferably 5 minutes to 1 hour.

When the protective group is substituted silyl, the protective group can also be removed under basic conditions (e.g., sodium hydroxide/water-containing ethanol, etc.) or in the presence of fluoride anion (e.g., $n\text{-}Bu_4N^+F^-$, $C_5H_5N^+HF^-$, etc.).

Since the compound (I-1) thus obtained has a high E-isomer/Z-isomer ratio in which the preferred E-isomer predominates, it can be used in the next step as the reaction mixture or crude product, or if necessary, after purifying it by conventional methods (e.g., column chromatography, recrystallization, etc.).

The compound (II-1) that can be used as the starting material of this reaction can preferably be prepared according to Scheme 2 below.

Scheme 2

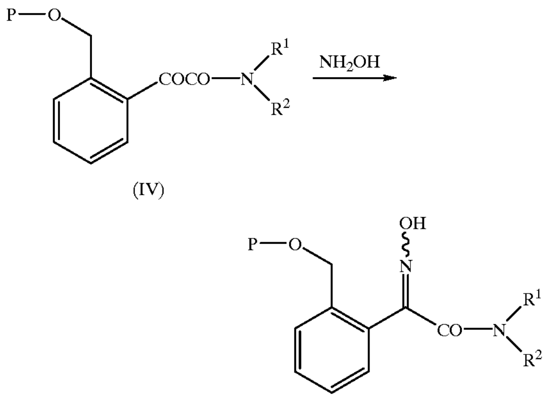

(IV)

(II-1)

wherein each symbol is as defined above.

That is, the compound (II-1) can be prepared by reacting the compound (IV) with hydroxylamine and/or its salt in an appropriate solvent.

The amount of the hydroxylamine to be used is 1 to 4 equivalents, preferably 1 to 3 equivalents, based on the compound (IV).

The hydroxylamine salts include, for example, salts with mineral acid such as hydrochloric acid, sulfuric acid, etc. When the hydroxylamine salts are used, the salts are neutralized with a base so as not to remove the protective group of hydroxyl. The bases that can be used include, for example, metal hydroxides (e.g., sodium hydroxide, potassium hydroxide, etc.), metal carbonates (e.g., sodium carbonate, potassium carbonate, etc), metal alkoxides (e.g., sodium methoxide, sodium ethoxide, etc.), amines (e.g., pyridine, etc.), etc. The amount of the base to be used is 1 to 3 equivalents, preferably 1 to 2 equivalents, based on the hydroxylamine salt.

The solvents that can be used include, for example, hydrocarbons (e.g., benzene, toluene, xylene, etc.), halogenated hydrocarbons (e.g., chloroform, 1,2-dichloroethane, etc.), ethers (e.g., tetrahydrofuran, dioxane, etc.), alcohols (e.g., methanol, ethanol, n-propanol, isopropanol, etc.), water, etc., and mixed solvent thereof.

The reaction temperature is 0 to 150° C., preferably 20 to 100° C. The reaction time is normally about 15 minutes to 24 hours.

The compound (II-1) thus obtained can be used in the next step as the reaction mixture or the crude product, or after purifying it by conventional methods (e.g., column chromatography, recrystallization, etc.).

The compound (I-2) can be prepared according to Scheme 3 below.

Scheme 3

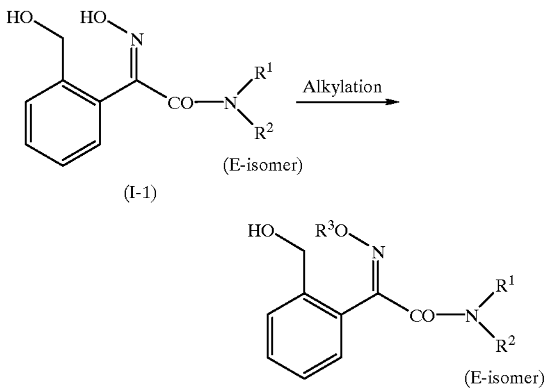

(I-1) (E-isomer) (I-2) (E-isomer)

wherein each symbol is as defined above.

That is, the compound (I-2) can be prepared by reacting the compound (I-1) with an alkylating agent in the presence of a base in an appropriate solvent to alkylate the compound (I-1).

The alkylating agents include, for example, dialkyl sulfates (e.g., di($C_{1-6}$ alkyl) sulfates such as dimethyl sulfate, diethyl sulfate, etc.), alkyl halides (e.g., $C_{1-6}$ alkyl halides such as methyl chloride, methyl bromide, methyl iodide, etc.), etc. The amount of the alkylating agent to be used is 1 to 10 mol, preferably 1 to 1.5 mol, per mol of the compound (I-1).

The solvents include, for example, ketones (e.g., acetone, ethyl methyl ketone, etc.), ethers (e.g., tetrahydrofuran, dioxane, etc.), hydrocarbons (e.g., toluene, benzene, hexane, cyclohexane, etc.), halogenated hydrocarbons (e.g., dichloromethane, 1,2-dichloroethane, etc.), alcohols (e.g., methanol, ethanol, etc.), water, etc., and mixed solvent thereof.

The bases include, for example, metal carbonates (e.g., sodium carbonate, potassium carbonate, etc.), metal hydroxides (e.g., sodium hydroxide, potassium hydroxide, lithium hydroxide, etc.), metal hydrides (e.g., sodium hydride, lithium hydride, etc.), etc. The amount of the base to be used is 1 to 10 mol, preferably 1 to 2 mol, per mol of the compound (I-1).

If necessary, this reaction can be carried out in the presence of a phase-transfer catalyst. The phase-transfer catalysts include, for example, quaternary ammonium salts [e.g., tetraalkylammonium halides (e.g., tetrabutylammonium chloride, tetrabutylammonium bromide, etc.), tetraalkylammonium hydrosulfates (e.g., tetrabutylammonium hydrosulfate, etc.), etc.], amines (e.g., tris(3,6-dioxaheptyl) amine, etc.), etc. The amount of the phase-transfer catalyst to be used is 0.01 to 1 mol, preferably 0.01 to 0.2 mol, per mol of the compound (I-1).

The reaction temperature is normally −20 to 100° C., preferably 0 to 50° C., and the reaction time is normally 1 to 24 hours.

The compound (I-2) thus obtained can be used in the next step as the reaction mixture or crude product, or after purifying it by conventional methods (e.g., column chromatography, recrystallization, etc.).

Alternatively, the compound (I-2) can be prepared according to Scheme 4 below.

Scheme 4

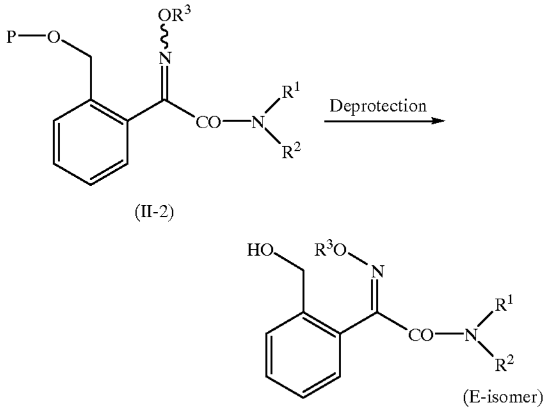

(II-2) (I-2) (E-isomer)

wherein each symbol is as defined above.

That is, the compound (I-2) can be prepared by removing the protective group (P) of hydroxyl of the compound (II-2).

In this reaction, the protective group of hydroxyl group is removed and the isomerization to the E-isomer proceeds at the same time. Therefore, a separate isomerization step to the E-isomer is not required, and the compound (I-2) can be obtained in high yield and purity.

This reaction can be carried out under the same reaction conditions as those of the reaction of Scheme 1.

The compound (I-2) thus obtained can be used in the next step as the reaction mixture or crude product, or after purifying it by conventional methods (e.g., column chromatography, recrystallization, etc.).

The compound (II-2) that can be used as the starting material of the reaction of Scheme 4 can preferably be prepared according to Scheme 5 below.

Scheme 5

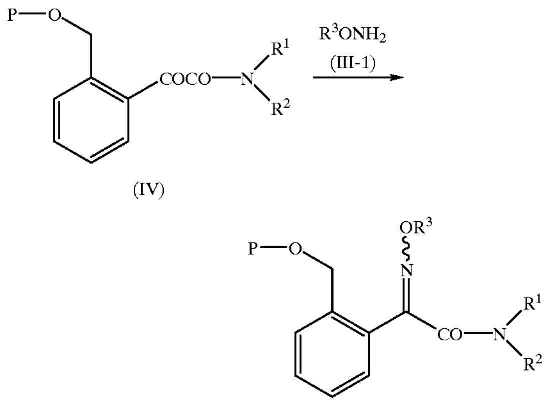

(IV) (II-2)

wherein each symbol is as defined above.

That is, the compound (II-2) can be prepared by reacting the compound (IV) with the compound (III-1) and/or its salts. The salts of the compound (III-1) include the same salts as those of the hydroxylamine of Scheme 2.

This reaction can be carried out under the same reaction conditions as those of the reaction of Scheme 2.

The compound (II-2) thus obtained can be used in the next step as the reaction mixture or crude product, or after purifying it by conventional methods (e.g., column chromatography, recrystallization, etc.).

The compound (IV) that can be used as the starting material in Scheme 2 or 5 can preferably be prepared according to Scheme 6 below.

Scheme 6

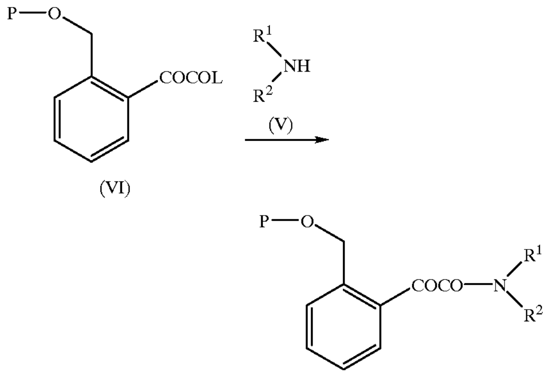

(VI)
(IV)

wherein L is a halogen atom or alkoxy, and the other symbols are as defined above.

That is, the compound (IV) can be prepared by reacting the compound (VI) with the compound (V).

The halogen atoms represented by L include fluorine, chlorine, bromine and iodine. In particular, chlorine and bromine are preferred.

The alkoxy represented by L includes alkoxy having 1 to 6 carbon atom, preferably 1 to 4 carbon atoms, such as methoxy, ethoxy, propoxy, etc.

The compound (V) is added dropwise to the compound (VI) without diluting the compound (V) with a solvent, or after diluting it with an appropriate solvent. Alternatively, the gaseous compound (V) is introduced into the compound (VI).

The amount of the compound (V) is 1 to 10 equivalents, preferably 1 to 5 equivalents, based on the compound (VI). When the compound (VI) is an α-ketoacid halide, the amount of the compound (V) is preferably 2 to 6 equivalents based on the compound (VI).

When an isolated a-ketoacid ester is used as the compound (VI), it is diluted with an appropriate solvent. The solvents include, for example, hydrocarbons (e.g., benzene, toluene, xylene, etc.), halogenated hydrocarbons (e.g., dichloromethane, 1,2-dichloroethane, etc.), ethers (e.g., tetrahydrofuran, dioxane, etc.), alcohols (e.g., methanol, ethanol, etc.), water, etc., and mixed solvents thereof.

The compound (V) is added dropwise or introduced at −75 to 50° C., preferably −60 to 30° C., over 5 minutes to 2 hours, preferably 15 minutes to 1 hour. Then, the reaction is carried out at −50 to 100° C., preferably −30 to 60° C., for 1 minute to 5 hours, preferably 10 minutes to 2 hours, to obtain the compound (IV).

The compound (IV) thus obtained can be used in the next step as the reaction mixture or crude product, or after purifying it by conventional methods (e.g., column chromatography, recrystallization, etc.).

The compound (VI) that can be used as the starting material in the reaction of Scheme 6 can preferably be prepared according to Scheme 7 below.

Scheme 7

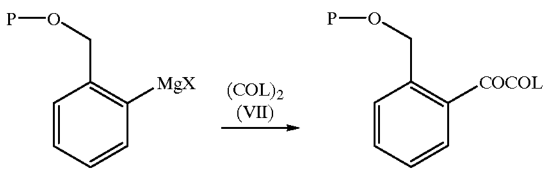

(VIII)
(VI)

wherein X is a halogen atom, and the other symbols are as defined above.

That is, the compound (VI) can be prepared by reacting the compound (VIII) with the compound (VII).

The halogen atoms represented by X include fluorine, chlorine, bromine, and iodine. In particular, chlorine, bromine or iodine is preferred.

Normally, a solution of the compound (VIII) is added dropwise to a solution of the compound (VII) in an appropriate solvent. The amount of the compound (VII) to be used is 1 to 4 equivalents, preferably 1 to 2 equivalents, based on the compound (VIII).

The addition is carried out at −100 to 50° C., preferably −70 to 30° C., over 5 minutes to 2 hours, preferably 15 minutes to 1 hour. Then, the reaction is carried out at −100 to 50° C., preferably −80 to 30° C., for 5 minutes to 2 hours, preferably 15 minutes to 1 hour.

The solvents include ethers such as THF, diethyl ether, dibutyl ether, etc., and hydrocarbons such as toluene.

Examples of the compound (VII) include oxalyl halides such as oxalyl chloride, oxalyl bromide, etc., oxalic acid esters such as dimethyl oxalate, diethyl oxalate, etc., alkyloxalyl chlorides such as methyloxalyl chloride, ethyloxalyl chloride, etc.

Alternatively, the compound (VII) which is not diluted or diluted with an appropriate solvent can be added dropwise to the compound (VIII) for the reaction. The solvent and the reaction conditions may be the same as those described above.

When the compound (VI) thus obtained is an α-ketoacid halide, it can be used in the next step as the reaction mixture. When it is an α-ketoacid ester, it can be used in the next step as the reaction mixture or crude product, or after purifying it by conventional methods (e.g., column chromatography, recrystallization, etc.).

Alternatively, when the compound (VI) is an α-ketoacid ester, the compound (VIII) in which the MgX is replaced with Li is used as the starting material and reacted with the compound (VII).

The compound of the formula (VI'):

(VI')

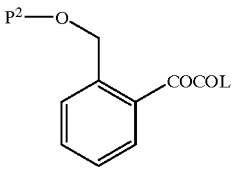

wherein each symbol is as defined above, included in the above compound (VI), is a novel compound and included in the present invention.

L is preferably alkoxy.

The compound (VIII) that can be used as the starting material of the reaction of Scheme 7 can preferably be prepared according to Scheme 8 below.

Scheme 8

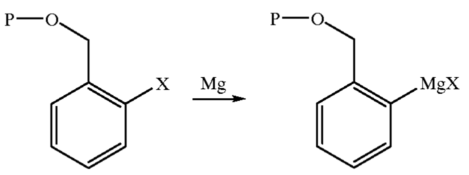

(IX) (VIII)

wherein each symbol is as defined above.

That is, the compound (VIII) can be prepared by reacting the compound (IX) with magnesium in an appropriate solvent.

Normally, magnesium in an amount of 1 to 4 equivalents, preferably 1 to 2 equivalents, based on the compound (IX) is reacted with the compound (IX).

The solvents to be used include ethers such as dry THF, diethyl ether, dibutyl ether, etc. These solvents can be used alone or as mixtures with other solvents such as hydrocarbons (e.g., toluene, etc.), amines (e.g., triethylamine, etc.), etc.

The reaction temperature is room temperature to 150° C., preferably 40 to 100° C. The reaction time is 10 minutes to 48 hours, preferably 30 minutes to 6 hours.

If necessary, a small amount of iodine, dibromoethane, ethyl bromide, etc., is used as an activator of the reaction. The amount of the activator is 0.001 to 0.4 equivalents, preferably 0.005 to 0.2 equivalents.

The compound (VIII) in which the MgX is replaced with Li can be prepared by reacting the compound (IX) with metal lithium or an alkyllithium (e.g., n-butyllithium, etc.).

The compound (VIII) thus obtained can be used in the next step as the reaction mixture or crude product.

The compound (IX) that can be used as the starting material of the reaction of Scheme 8 can preferably be prepared according to Scheme 9.

Scheme 9

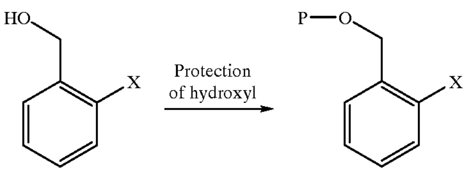

(X) (IX)

wherein each symbol is as defined above.

That is, the compound (IX) can be prepared by protecting the hydroxyl of the commercially available compound (X) with an appropriate protective group.

The hydroxyl can be protected by conventional protection methods of hydroxyl, for example, by those described in T. W. Green, "Protective Groups in Organic Synthesis", p. 1–113, John Willy & Sons (1981); C. B. Reese, "Protective Groups in Organic Chemistry", edited by J. F. McOmie, p. 95–143, Plenum Press (1973).

For example, the compound (IX) protected with tetrahydropyranyl, tetrahydrothiopyranyl, tetrahydrofuranyl, tetrahydrothiofuranyl, 1-ethoxyethyl or 1-methyl-1-methoxyethyl can be prepared by reacting the corresponding olefins with the compound (X) in the presence of an acid catalyst in an appropriate solvent or in the absence of a solvent.

The corresponding olefins are 3,4-dihydro-2H-pyran, 2,3-dihydro-4H-thiin, dihydrofuran, dihydrothiofuran, ethyl vinyl ether and 2-methoxypropene, respectively. These compounds are commercially available or can be prepared by known methods.

The amount of the olefin to be used is 1 to 3 equivalents, preferably 1 to 2 equivalents, based on the compound (X).

The acid catalysts include, for example, hydrogen chloride, phosphorus oxychloride, p-toluenesulfonic acid, p-toluenesulfonic acid pyridine salt, montmorillonite, bistrimethyl sulfate, acetic acid, pyridinium polyvinyl p-toluenesulfonate, trifluoroacetic acid, boron trifluoride etherate ($BF_3$•$OEt_2$), acidic ion exchange resins, etc.

When the solvent is used, a non-alcoholic solvent can be used. Examples of the solvents include hydrocarbons (e.g., benzene, toluene, xylene, etc.), halogenated hydrocarbons (e.g., chloroform, dichloromethane, etc.), ethers (e.g., diethyl ether, tetrahydrofuran, dioxane, etc.), esters (e.g., ethyl acetate, etc.), N,N-dimethylformamide, etc., and mixture thereof.

The reaction temperature is −30 to 100° C., preferably 0 to 60° C.

The reaction time is normally about 15 minutes to 24 hours.

The silyl ether compound (IX) can be obtained by reacting the compound (X) with an appropriate silylating agent. In general, chlorosilane is used as the silylating agent, and reacted with the compound (X) in the presence of a base in an appropriate solvent.

The chlorosilane is commercially available or can be prepared by known methods.

The amount of the chlorosilane to be used is 1 to 5 equivalents, preferably 1 to 2 equivalents, based on the compound (X). The bases to be used include organic bases (e.g., N,N-dimethylaniline, pyridine, triethylamine, imidazole, etc.), metal carbonates (e.g., sodium carbonate, potassium carbonate, etc.), metal hydrides (e.g., sodium hydride, potassium hydride, etc.), metal bicarbonates (e.g., sodium bicarbonate, potassium bicarbonate, etc.), etc. The amount of the base to be used is 1 equivalent or more, preferably 1 to 2 equivalents.

The solvents to be used include hydrocarbons (e.g., hexane, benzene, toluene, xylene, etc.), halogenated hydrocarbons (e.g., chloroform, dichloromethane, etc.), ethers (e.g., diethyl ether, tetrahydrofuran, dioxane, etc.), ketones (e.g., acetone, methyl ethyl ketone, etc.), nitrites (e.g., acetonitrile, etc.), N,N-dimethylformamide, dimethylsulfoxide, etc., and mixed solvent thereof.

The reaction temperature is −20 to 100° C., preferably 0 to 60° C.

The reaction time is 5 minutes to 30 hours, preferably 30 minutes to 15 hours.

The compound (IX) protected with methoxymethyl or triphenylmethyl and the above compound (IX) protected with tetrahydrofuranyl or 1-ethoxyethyl can be obtained by reacting the corresponding halides with the compound (X) in the presence of a base.

The corresponding halides are halomethyl methyl ethers, triphenylmethyl halides, 2-halotetrahydrofurans and 1-haloethylethers, respectively. These compound are commercially available or can be prepared by known methods.

As the halides, chlorides or bromides can be used.

The amount of the halide to be used, the kinds of bases and solvents, and the reaction conditions, etc., are the same as those of the reaction between the above chlorosilane and the compound (X).

The above compound (IX) protected with methoxymethyl can also be obtained by reacting the compound (X) with dimethoxymethane in the presence of an appropriate catalyst (e.g., phosphorus pentaoxide, etc.).

The solvents to be used and the reaction conditions are the same as those of the above reaction between the olefin and the compound (X).

The compound (IX) thus obtained can be used in the next step as the crude product or after purifying it by conventional methods (e.g., column chromatography, recrystallization, etc.).

The compound of the formula (IX'):

(IX')

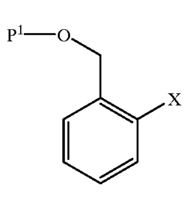

wherein X is a halogen atom, $P^1$ is aralkyl, triaralkylsilyl, alkoxyalkyl, alkoxyalkoxyalkyl, alkylthioalkyl, tetrahydropyranyl, tetrahydrothiopyranyl, tetrahydrofuranyl, tetrahydrothiofuranyl or aralkyloxyalkyl, included in the above compound (IX), is a novel compound and included in the present invention. Examples of each group represented by $P^1$ are the same as those represented by P.

The compound (I-2) obtained in the reactions of Schemes 3 and 4 can conveniently be converted to the alkoxyiminoacetamide compound (XI) that has potent fungicidal activity and is useful as an agricultural fungicide, for example, according to Scheme 10 below (JP-A 3-246268, JP-A 4-182461). Thus, the compound (I-2) is important as an intermediate for the production.

Scheme 10

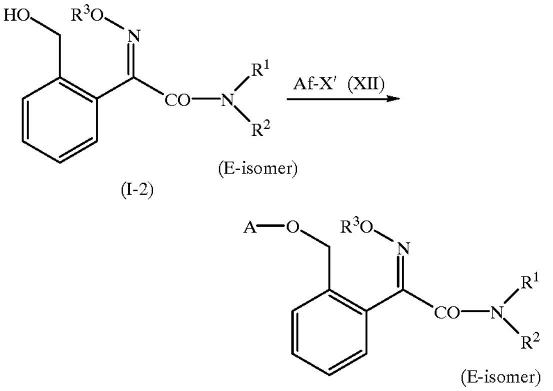

(I-2) (E-isomer)

(XI) (E-isomer)

wherein A is optionally substituted phenyl or an optionally substituted heterocyclic group, X' is as defined as X, and the other symbols are as defined above.

That is, the compound (I-2) is reacted with the compound (XII) according to JP-A 3-246268 or JP-A 4-182461 to obtain the compound (XI).

The phenyl represented by A includes substituted or unsubstitued phenyl. The heterocyclic groups represented by A include, for example, heterocyclic groups containing at least one ring-constituting heteroatom selected from nitrogen, oxygen and sulfur, such as pyridyl, pyrimidinyl, oxazolyl, thiazolyl, pyrazolyl, imidazolyl, isoxazolyl, isothiazolyl, quinolyl, etc. When these groups are substituted, preferred examples of the substituent include methyl, trifluoromethyl, trichloromethyl, fluorine, chlorine, methoxy, etc.

EXAMPLES

The following examples and reference examples further illustrate the present invention in detail, but are not to be construed to limit the scope of the invention.

Example 1

Preparation of 1-bromo-2-(1-ethoxyethyl) oxymethyl-benzene

Pyridinium p-toluenesulfonate (0.50 g, 0.002 mol) was added to a mixed solution of 2-bromobenzyl alcohol (18.70 g, 0.1 mol), dichloromethane (150 ml) and ethyl vinyl ether (14.42 g, 0.2 mol) under ice-cooling, and the mixture was stirred at room temperature for 3 hours. After completion of the reaction, a half-saturated aqueous solution (300 ml) of sodium bicarbonate was added, and the mixture was extracted with dichloromethane (100 ml) twice. The extract was dried over anhydrous magnesium sulfate and concentrated under reduced pressure to obtain 1-bromo-2-(1-ethoxyethyl)oxymethyl-benzene (25.44 g, Yield: 98.2%) as a colorless oil.

$^1$H-NMR ($CDCl_3$) δ ppm: 1.22(3H,t,J=7.3), 1.41 (3H,t, J=5.5), 3.49–3.77(2H,m), 4.59(1H,d,J=12.8), 4.70 (1H,d,J=12.8), 4.87(1H,q,J=5.5), 7.11–7.55(4H,m).

Example 2

Preparation of 1-bromo-2-(2-tetrahydropyranyloxymethyl)benzene

Pyridinium p-toluenesulfonate (0.30 g, 0.0012 mol) was added to a solution of 2-bromobenzyl alcohol (25 g, 0.134 mol) in dichloromethane (100 ml), and the mixture was stirred at room temperature. To this mixture was added 3,4-dihydro-2H-pyrane (16.86 g, 0.20 mol). After the resulting mixture was stirred at room temperature for 2 hours, a saturated aqueous solution (200 ml) of sodium bicarbonate was added. The mixture was extracted with dichloromethane (200 ml). After the mixture was dried over anhydrous magnesium sulfate, the solvent was evaporated to obtain the desired compound 1-bromo-2-(2-tetrahydropyranyloxymethyl)benzene (36.00 g, Yield: 99.3%) as an oil.

$^1$H-NMR ($CDCl_3$) δ ppm: 1.45–1.80(6H,m), 3.45–3.55 (1H,m), 3.80–3.90(1H,m), 4.52(1H,d,J=15.0), 4.80(1H,m), 4.90(1H,d,J=15.0), 7.16(1H,t,J=7.3), 7.31(1H,t,J=7.3), 7.51 (1H,d,J=7.3), 7.54(1H,d,J=7.3).

Example 3

Preparation of ethyl 2-[2-{(1-ethoxyethyl) oxymethyl}phenyl]-2-oxoacetate

A mixed solution of 1-bromo-2-(1-ethoxyethyl) oxymethylbenzene (3.11 g, 0.012 mol) and dry THF (10 ml) was added dropwise at 50 to 60° C. over 25 minutes to a solution prepared by adding dry THF (2 ml) and ethyl bromide (0.2 ml) to magnesium (0.44 g, 0.018 mol) in a stream of nitrogen. After completion of the addition, the mixture was stirred at 50 to 60° C. for 1 hour and cooled to room temperature. After cooling, the mixture was added dropwise to a mixed solution of ethyl oxalate (2.63 g, 0.018 mol) and dry THF (30 ml) at below −50° C. over 15 minutes. Then, the mixture was stirred at −50 to −60° C for 1 hour. After completion of the reaction, water (200 ml) was added, and the mixture was extracted with ether (200 ml). The extract was dried over anhydrous magnesium sulfate and concentrated under reduced pressure. The resulting residue was purified by silica gel chromatography (ethyl acetate/n-hexane) to obtain ethyl 2-[2-{(1-ethoxyethyl)oxymethyl}phenyl]-2-oxoacetate (2.30 g, Yield: 68.4%) as a colorless oil.

$^1$H-NMR ($CDCl_3$) δ ppm: 1.19(3H,t,J=7.3), 1.36 (3H,d, J=5.5), 1.41(3H,t,J=7.3), 3.47–3.68(2H,m), 4.42 (2H,q,J=7.3), 4.78–5.01(3H,m), 7.32–7.71(4H,m).

Example 4

Preparation of ethyl 2-oxo-2-[2-(2-tetrahydropyranyloxymethyl)phenyl]acetate

Magnesium (2.67 g, 0.11 mol) and bromoethane (0.2 ml) were added to a mixed solution of 1-bromo-2-(2-tetrahydropyranyloxymethyl)benzene (27.11 g, 0.10 mol) and THF (50 ml) under an atmosphere of nitrogen gas. The mixture was stirred at room temperature for 1 hour to prepare a Grignard reagent. The Grignard reagent was added dropwise to a mixed solution of diethyl oxalate (29.23 g, 0.20 mol) and THF (100 ml) cooled to −78° C. The mixture was stirred at −78° C. for 1 hour, water (150 ml) was added, and the mixture was extracted with ether (200 ml). The extract was dried over anhydrous magnesium sulfate and concentrated under reduced pressure. The resulting residue was purified by silica gel chromatography (ethyl acetate/n-hexane) to obtain ethyl 2-oxo-2-[2-(2-tetrahydropyranyloxymethyl)phenyl]acetate (22.60 g, Yield: 77.3%) as a colorless oil.

$^1$H-NMR ($CDCl_3$) δ ppm: 1.38(3H,t,J=7.0), 1.40–1.85 (6H,m), 3.50–3.60(1H,m), 3.80–3.90(1H,m), 4.32–4.40(2H, m), 4.69(1H,m), 4.85(1H,d,J=14.6), 5.09(1H,d,J=14.6), 7.43 (1H,t, J=7.3), 7.58–7.70(3H,m).

Example 5

Preparation of 2-[2-{(1-ethoxyethyl)oxymethyl}phenyl]-N-methyl-2-oxoacetamide

A 40% methylamine-methanol solution (1.63 g, 0.021 mol) was added to a mixed solution of ethyl 2-[2-{(1-ethoxyethyl)oxymethyl}phenyl]-2-oxoacetate (1.96 g, 0.007 mol) and THF (7 ml) under ice-cooling. The mixture was stirred at room temperature for 1 hour. After completion of the reaction, water (100 ml) was added, and the mixture was extracted with dichloromethane (80 ml) twice. The extract was dried over anhydrous magnesium sulfate and concentrated under reduced pressure. The resulting residue was purified by silica gel chromatography (ethyl acetate/n-hexane) to obtain 2-[2-{(1-ethoxyethyl)oxymethyl}phenyl]-N-methyl-2-oxoacetamide (1.35 g, Yield: 72.7%) as a colorless oil.

$^1$H-NMR ($CDCl_3$) δ ppm: 1.17(3H,t,J=7.3), 1.29(3H,d, J=4.9), 2.96(3H,d,J=5.5), 3.41–3.63(2H,m), 4.70–4.92(3H, m), 7.04(1H,brs), 7.33–7.84(4H,m).

Example 6

Preparation of 2-[2-{(1-ethoxyethyl)oxymethyl}phenyl]-N-methyl-2-oxoacetamide

A mixed solution of 1-bromo-2-(1-ethoxyethyl)oxymethylbenzene (7.77 g, 0.03 mol) and dry THF (27 ml) was added dropwise at 50 to 60° C. over 30 minutes to a solution prepared by adding dry THF (3 ml) and ethyl bromide (0.2 ml) to magnesium (1.09 g, 0.045 mol) in a stream of nitrogen. After completion of the addition, the mixture was stirred at 50 to 60° C. for 1 hour and cooled to room temperature. After cooling, the mixture was added dropwise to a mixed solution of ethyl oxalate (6.58 g, 0.045 mol) and dry THF (50 ml) at below −60° C. over 15 minutes. Then, the mixture was stirred at −60 to −70° C. for 1 hour. A 40% methylamine-methanol solution (11.65 g, 0.15 mol) was added to the reaction mixture, and the temperature of the mixture was raised from −50° C. to room temperature over 1 hour. After completion of the reaction, water (500 ml) was added, and the mixture was extracted with ether (300 ml), followed by dichloromethane (300 ml). The extract was combined, dried over anhydrous magnesium sulfate and concentrated under reduced pressure. The resulting residue was purified by silica gel chromatography (ethyl acetate/n-hexane) to obtain 2-[2-{(1-ethoxyethyl)oxymethyl}phenyl]-N-methyl-2-oxoacetamide (3.83 g, Yield: 48.1%) as a colorless oil.

Example 7

Preparation of N-methyl-2-oxo-2-[2-(2-tetrahydropyranyloxymethyl)phenyl]acetamide A 40% methylamine-methanol solution (2.65 g, 0.0341 mol) was added to a mixed solution of ethyl 2-oxo-2-[2-(2-tetrahydropyranyloxymethyl)phenyl]acetate (2.00 g, 0.0068 mol) and methanol (20 ml). The mixture was stirred at room temperature for 2 hours. After completion of the reaction, the mixture was concentrated under reduced pressure. The resulting residue was purified by silica gel chromatography (ethyl acetate/n-hexane) to obtain N-methyl-2-oxo-2-[2-(2-tetrahydropyranyloxymethyl)phenyl]acetamide (1.30 g, Yield: 69.0%) as a colorless oil.

$^1$H-NMR ($CDCl_3$) δ ppm: 1.49–1.80(6H,m), 2.96(3H,d, J=4.9), 3.47–3.52(1H,m), 3.77–3.86(1H,m), 4.62(1H,t,J=3.1), 4.76(1H,d,J=13.4), 4.98(1H,d,J=13.4), 7.06(1H,brs), 7.34–7.80(4H,m).

Example 8

Preparation of N-methyl-2-oxo-2-[2-(2-tetrahydropyranyloxymethyl)phenyl]acetamide A mixed solution of 1-bromo-2-(2-tetrahydropyranyloxymethyl)benzene (2.71 g, 0.01 mol) and dry THF (8 ml) was added dropwise at 50 to 60° C. over 20 minutes to a solution prepared by adding dry THF (2 ml) and ethyl bromide (0.1 ml) to magnesium (0.36 g, 0.015 mol) in a stream of nitrogen. After completion of the addition, the mixture was stirred at 50 to 60° C. for 1 hour and cooled to room temperature. After cooling, the mixture was added dropwise to a mixed solution of oxalyl chloride (1.90 g, 0.015 mol) and dry THF (30 ml) at below −50° C. over 15 minutes. Then, the mixture was stirred at −60 to −70° C. for 40 minutes. A 40% methylamine-methanol solution (4.66 g, 0.06 mol) was added to the reaction mixture, and the mixture was stirred at −20 to −10° C. for 30 minutes. After completion of the reaction, water (150 ml) was added, and the mixture was extracted with ether (150 ml). The extract was washed with saturated brine, dried over anhydrous magnesium sulfate and concentrated under reduced pressure. The resulting residue was purified by silica gel chromatography (ethyl acetate/n-hexane) to obtain N-methyl-2-oxo-2-[2-(2-tetrahydropyranyloxymethyl)phenyl]acetamide(1.18 g, Yield: 42.5%) as a colorless oil.

Example 9

Preparation of N-methyl-2-oxo-2-[2-(2-tetrahydropyranyloxymethyl)phenyl]acetamide A mixed solution of 1-bromo-2-(2-tetrahydropyranyloxymethyl)benzene (2.71 g, 0.01 mol) and dry THF (8 ml) was added dropwise at 50 to 60° C. over 20 minutes to a solution prepared by adding dry THF (2 ml) and ethyl bromide (0.1 ml) to magnesium (0.36 g, 0.015 mol) in a stream of nitrogen. After completion of the addition, the mixture was stirred at 50 to 60° C. for 1 hour and cooled to room temperature. After cooling, the mixture was added dropwise to a mixed solution of ethyl oxalate (2.19 g, 0.015 mol) and dry THF (20 ml) at below −60° C. over 10 minutes. Then, the mixture was stirred at −60 to −70° C. for 1 hour. A 40% methylamine-methanol solution (3.88 g, 0.05 mol) was added to the reaction mixture, and the temperature of the mixture was raised from −50° C. to room temperature over 1 hour. After completion of the reaction, water (200 ml) was added, and the mixture was extracted with ether (200 ml). The extract was washed with saturated brine, dried over anhydrous magnesium sulfate and concentrated under reduced pressure. The resulting residue was purified by silica gel chromatography (ethyl acetate/n-hexane) to obtain N-methyl-2-oxo-2-[2-(2-tetrahydropyranyloxymethyl) phenyl]acetamide (1.21 g, Yield: 43.6%) as a colorless oil.

Example 10

Preparation of 2-[2-{(1-ethoxyethyl) oxymethyl}phenyl]-2-hydroxyimino-N-methylacetamide Methanol (4 ml) and 50% aqueous hydroxylamine solution (0.4 g, 0.006 mol) were added to 2-[2-{(1-ethoxyethyl) oxymethyl}phenyl]-N-methyl-2-oxoacetamide (0.53 g, 0.002 mol). The mixture was stirred under reflux for 5 hours. After completion of the reaction, water (100 ml) was added, and the mixture was extracted with dichloromethane (50 ml) twice. The extract was dried over anhydrous magnesium sulfate and concentrated under reduced pressure. The resulting residue was purified by silica gel chromatography (ethyl acetate/n-hexane) to obtain 2-[2-{(1-ethoxyethyl) oxymethyl}phenyl]-2-hydroxyimino-N-methylacetamide (Isomer A: 0.21 g (Yield: 37.5%), colorless oil; Isomer B: 0.14 g (Yield: 25.0%), colorless crystals).

Isomer A:

$^1$H-NMR ($CDCl_3$) δ ppm: 1.67(3H,t,J=7.3), 1.30(3H,d, J=5.5), 2.82(3H,d,J=5.5), 3.42-3.63(2H,m), 4.54(1H,d,J=11.6), 4.66(1H,d,J=11.6), 4.73(1H,q,J=5.5), 6.00(1H,brs), 7.30–7.49(4H,m).

Isomer B: mp 85–87° C.

$^1$H-NMR ($CDCl_3$) δ ppm: 1.16(3H,t,J=7.3), 1.28(3H,d, J=4.9), 2.90(3H,d,J=4.9), 3.44–3.61(2H,m), 4.44(1H,d,J=12.8), 4.58(1H,d,J=12.8), 4.71(1H,q,J=5.5), 6.72(1H,brs), 7.18–7.51(4H,m), 8.30(1H,brs).

Example 11

Preparation of 2-[2-{(1-ethoxyethyl)oxymethyl}-phenyl]-2-methoxyimino-N-methylacetamide Methoxyamine hydrochloride (0.50 g, 0.006 mol) was dissolved in methanol (6 ml), and a 28% sodium methoxide-methanol solution (1.45 g, 0.0075 mol) was added to the solution to obtain a suspension. A mixed solution of 2-[2-{(1-ethoxyethyl)oxymethyl}phenyl]-N-methyl-2-oxoacetamide (0.80 g, 0.003 mol) and methanol (3 ml) was added to the suspension, and the mixture was stirred under reflux for 1 hour. After completion of the reaction, half-saturated brine (150 ml) was added, and the mixture was extracted with dichloromethane (100 ml) twice. The extract was dried over anhydrous magnesium sulfate and concentrated under reduced pressure. The resulting residue was purified by silica gel chromatography (ethyl acetate/n-hexane) to obtain an E/Z mixture of 2-[2-{(1-ethoxyethyl) oxymethyl}phenyl]-2-methoxyimino-N-methylacetamide (0.82 g, Yield: 92.8%) as a colorless oil.

$^1$H-NMR ($CDCl_3$) δ ppm: 1.18(1.20)(3H,t,J=7.3), 1.28 (1.33)(3H,d,J=5.5), 2.87(2.91)(3H,d,J=4.9), 3.41–6.64(2H, m), 3.95(4.00)(3H,s), 4.36–4.83(3H,m), 6.76(7.01) (1H, brs), 7.14–7.49(4H,m).

Example 12

Preparation of 2-methoxyimino-N-methyl-2-[2-(2-tetrahydropyranyloxymethyl)phenyl]acetamide Methoxyamine hydrochloride (0.33 g, 0.004 mol) was dissolved in methanol (4 ml), and pyridine (0.47 g, 0.006 mol) was added to the solution. To the mixture was added a mixed solution of N-methyl-2-oxo-2-[2-(2-tetrahydropyranyloxymethyl)phenyl]acetamide (0.55 g, 0.002 mol) and methanol (2 ml). The mixture was stirred under reflux for 2 hours. After completion of the reaction, half-saturated brine (100 ml) was added, and the mixture was extracted with dichloromethane (80 ml) twice. The extract was dried over anhydrous magnesium sulfate and concentrated under reduced pressure. The resulting residue was purified by silica gel chromatography (ethyl acetate/n-hexane) to obtain an E/Z mixture of2-methoxyimino-N-methyl-2-[2-(2-tetrahydropyranyloxymethyl)phenyl] acetamide (0.37 g, Yield: 60.4%) as a colorless oil.

$^1$H-NMR ($CDCl_3$) δ ppm: 1.43–1.90(6H,m), 2.87(2.91) (3H,d,J=4.9), 3.44–3.60(1H,m), 3.78–3.91(1H,m), 3.94 (4.01) (3H,s), 4.36–4.94(3H,m), 6.75(7.00)(1H,brs), 7.15–7.48(4H,m).

Example 13

Preparation of 2-(2-hydroxymethylphenyl)-2-methoxyimino-N-methylacetamide

Hydroxylamine hydrochloride (0.28 g, 0.004 mol) was dissolved in methanol (4 ml), and a 28% sodium methoxide-methanol solution (0.96 g, 0.005 mol) was added to obtain a suspension. A mixed solution of 2-{2-[(1-ethoxyethyl) oxymethyl]phenyl}-N-methyl-2-oxoacetamide (0.53 g, 0.002 mol) and methanol (2 ml) were added to the suspension. The mixture was stirred under reflux for 2 hours. After completion of the reaction, half-saturated brine (150 ml) was added, and the mixture was extracted with dichloromethane (100 ml) twice. The extract was dried over anhydrous magnesium sulfate and concentrated under reduced pressure to obtain a crude product of 2-[2-(1-ethoxyethyl)oxymethyl] phenyl-2-hydroxyimino-N-methylacetamide. Methanol (4 ml) and pyridinium p-toluenesulfonate (0.05 g, 0.0002 mol) were added to the crude product thus obtained, and the mixture was stirred under reflux for 30 minutes. After completion of the reaction, the mixture was concentrated, and acetone (4 ml) was added to the residue. Then, potassium carbonate (0.41 g, 0.003 mol) and dimethyl sulfate (0.30 g, 0.0024 mol) were added under ice-cooling, and the mixture was stirred at room temperature overnight. After completion of the reaction, the insoluble materials were filtered off, and the filtrate was concentrated under reduced pressure. The residue was purified by silica gel chromatography (ethyl acetate/n-hexane) to obtain 2-(2-hydroxymethylphenyl)-2-methoxyimino-N-methylacetamide (0.24 g, Yield: 54.0%, E 100%) as a colorless oil. A part of it was recrystallized from ethyl acetate/n-hexane to obtain crystals (mp 107–108° C.).

$^1$H-NMR ($CDCl_3$) δ ppm: 2.95(3H,d,J=4.9), 3.13(1H,t, J=6.1), 3.96(1H,s), 4.40(2H,d,J=6.1), 6.95(1H,brs), 7.11–7.55(4H,m)

Example 14

Preparation of 2-(2-hydroxymethylphenyl)-2-methoxyimino-N-methylacetamide

Methanol (4 ml) and pyridinium p-toluenesulfonate (0.04 g, 0.00017 mol) were added to an E/Z mixture of 2-[2-{(1-ethoxyethyl)oxymethyl}phenyl]-2-methoxyimino-N-methylacetamide (0.50 g, 0.0017 mol), and the mixture was stirred under reflux for 2 hours. After completion of the reaction, half-saturated brine (100 ml) was added, and the mixture was extracted with dichloromethane (50 ml) twice. The extract was dried over anhydrous magnesium sulfate and concentrated under reduced pressure. The resulting residue was purified by silica gel chromatography (ethyl acetate/n-hexane) to obtain 2-(2-hydroxymethylphenyl)-2-methoxyimino-N-methylacetamide (0.34 g, Yield: 90.0%, E/Z=96/4) as a colorless oil.

Example 15

Preparation of 2-(2-hydroxymethylphenyl)-2-methoxyimino-N-methylacetamide

Methanol (2 ml) and a 36% aqueous hydrochloric acid solution (0.01 g, 0.0001 mol) were added to an E/Z mixture of 2-methoxyimino-N-methyl-2-[2-(2-tetrahydropyranyloxymethyl)phenyl]acetamide (0.31 g, 0.001 mol), and the mixture was stirred at room temperature for 30 minutes. After completion of the reaction, half-saturated brine (80 ml) was added, and the mixture was extracted with dichloromethane (50 ml) twice. The extract was dried over anhydrous magnesium sulfate and concentrated under reduced pressure. The resulting residue was purified by silica gel chromatography (ethyl acetate/n-hexane) to obtain 2-(2-hydroxymethylphenyl)-2-methoxyimino-N-methylacetamide (0.21 g, Yield: 94.6%, E/Z=97/3) as colorless crystals.

Example 16

Preparation of 2-(2-hydroxymethylphenyl)-2-methoxyimino-N-methylacetamide

Methoxyamine hydrochloride (0.22 g, 0.0026 mol) was dissolved in methanol (2 ml), and a 28% sodium methoxide-methanol solution (0.58 g, 0.003 mol) was added to the solution to obtain a suspension. A mixed solution of 2-[2-{(1-ethoxyethyl)oxymethyl}phenyl)-N-methyl-2-oxoacetamide (0.53 g, 0.002 mol) and methanol (2 ml) was added to the suspension. The mixture was stirred under ref lux for 3 hours, and then cooled to room temperature. After cooling, p-toluenesulfonic acid monohydrate (0.19 g, 0.001 mol) was added, and the mixture was stirred at room temperature for 1 hour. After completion of the reaction, half-saturated brine (80 ml) was added, and the mixture was extracted with dichloromethane (50 ml) twice. The extract was dried over anhydrous magnesium sulfate and concentrated under reduced pressure. The resulting residue was purified by silica gel chromatography (ethyl acetate/n-hexane) to obtain 2-(2-hydroxymethylphenyl)-2-methoxyimino-N-methylacetamide (0.37 g, Yield: 83.2%, E/Z=97/3) as colorless crystals.

Example 17

Preparation of N-methyl-2-oxo-2-(2-(2-tetrahydropyranyloxymethyl)phenyl]acetamide Pyridinium p-toluenesulfonate (6.70 g, 0.027 mol) and 3,4-dihydro-2H-pyran (97.6 ml, 1.067 mol) were added to a solution of 2-bromobenzylalcohol (100.9 g, 0.539 mol) in dichloromethane (500 ml), and the mixture was stirred at room temperature for 70 hours. After completion of the reaction, the mixture was washed with water (200 ml) twice. The organic layer was dried over anhydrous magnesium sulfate and concentrated under reduced pressure to obtain an oil (152.11 g).

A mixed solution of the crude 1-bromo-2-(2-tetrahydropyranyloxymethyl)benzene thus obtained and dry THF (100 ml) was added dropwise in a stream of nitrogen at 50 to 55° C. over 45 minutes to a solution prepared by adding dry THF (50 ml) and ethyl bromide (1 ml) to magnesium (16.8 g, 0.70 mol). After completion of the addition, dry THF (200 ml) was added. The mixture was stirred at 55° C. for 30 minutes and cooled to room temperature. After cooling, the mixture was added dropwise to a mixed solution of ethyl oxalate (118.6 g, 0.80 mol) and dry THF (400 ml) at −65 to −70° C. over 1 hour, and the resulting mixture was stirred at −78° C. for 1 hour. Water (300 ml) and a saturated aqueous solution (80 ml) of ammonium chloride were added, and the mixture was stirred. Then, the organic layer and the aqueous layer were separated from each other, and the aqueous layer was extracted with ether (500 ml). The organic layer was combined, washed with saturated brine, dried over anhydrous magnesium sulfate and concentrated under reduced pressure to obtain an oil (214.7 g).

A 40% methylamine-methanol solution (167.4 g, 2.156 mol) was added to a mixed solution of the crude ethyl a-oxo-2-(2-tetrahydropyranyloxymethyl)phenylacetate thus obtained and methanol (100 ml), and the mixture was stirred at room temperature for 40 minutes. After completion of the reaction, the mixture was concentrated under reduced pressure. Benzene (300 ml) was added to the resulting residue to filter off the insoluble materials, and the filtrate was concentrated under reduced pressure. The resulting residue was purified by silica gel chromatography (ethyl acetate/n-hexane) to obtain N-methyl-2-oxo-2-[2-(2-tetrahydropyranyloxymethyl)phenyl]acetamide (114.8 g, Yield: 76.8%) as an oil.

Example 18

Preparation of 2-[2-{(1-ethoxyethyl) oxymethyl}phenyl]-N-methyl-2-oxoacetamide

A mixed solution of 1-bromo-2-(1-ethoxyethyl) oxymethylbenzene (25.92 g, 0.1 mol) and dry THF (90 ml) was added dropwise at 50 to 55° C. over 40 minutes to a solution prepared by adding dry THF (10 ml) and ethyl bromide (0.2 ml) to magnesium (3.65 g, 0.15 mol) in a stream of nitrogen. After completion of the addition, the mixture was stirred at 50 to 55° C. for 1 hour and cooled to room temperature. After cooling, the mixture was added dropwise to a mixed solution of ethyl oxalate (21.92 g, 0.15 mol) and dry THF (100 ml) at −70 to −65° C. over 1 hour. Then, the mixture was stirred at −75 to −70° C. for 1 hour. After completion of the reaction, water (200 ml) and a saturated aqueous solution (100 ml) of ammonium chloride were slowly added, and the mixture was extracted with ether (300 ml). The extract was dried over anhydrous magnesium sulfate and concentrated under reduced pressure. The resulting residue was dissolved in methanol (100 ml), and an aqueous 40% methylamine (23.30 g, 0.3 mol) solution was added under ice-cooling. The mixture was stirred at room temperature for 2 hours. After completion of the reaction, water (300 ml) was added, a part of the methanol was evaporated under reduced pressure, and the residue was extracted with ethyl acetate (300 ml). The extract was washed with saturated brine (300 ml), dried over anhydrous magnesium sulfate and concentrated under reduced pressure. The resulting residue was purified by silica gel chromatography (ethyl acetate/n-hexane) to obtain 2-[2-{(1-ethoxyethyl)oxymethyl}phenyl]-N-methyl-2-oxoacetamide (19.11 g, Yield: 72.0%) as a colorless oil.

Example 19

Preparation of 2-(2-hydroxymethylphenyl)-2-methoxyimino-N-methylacetamide

Methoxyamine hydrochloride (7.52 g, 0.09 mol) was dissolved in methanol (60 ml), and a 28% sodium methoxide-methanol solution (19.68 g, 0.102 mol) was added to the solution under ice-cooling to obtain a suspension. A solution of 2-[2-{(1-ethoxyethyl)oxymethyl}phenyl]-N-methyl-2-oxoacetamide (15.92 g, 0.06 mol) in methanol (60 ml) was added to the suspension. The mixture was stirred under reflux for 2 hours. After completion of the reaction, about half of the methanol was evaporated under reduced pressure, water (400 ml) was added, and the mixture was extracted with dichloromethane (200 ml) twice. The extract was dried over anhydrous magnesium sulfate and concentrated under reduced pressure. The resulting residue was dissolved in methanol (30 ml), a 36% aqueous hydrochloric acid solution (0.61 g, 0.006 mol) was added under ice-cooling, and the mixture was stirred for 0.5 hours. After completion of the reaction, water (370 ml) and saturated sodium bicarbonate (30 ml) were added, and the mixture was extracted with dichloromethane (200 ml) twice. The extract was dried over anhydrous magnesium sulfate and concentrated under reduced pressure to obtain crude 2-(2-hydroxymethylphenyl)-2-methoxyimino-N-methylacetamide (12.98 g, Yield: 97.3%, E/Z=96/4) as colorless crystals.

Reference Example 1

Synthesis of (E)-2-[2-(5-chloro-3-trifluoromethylpyridin-2-yloxymethyl)phenyl]-2-methoxyimino-N-methylacetamide 2-(2-Hydroxymethylphenyl)-2-methoxyimino-N-methylacetamide (300 mg) was dissolved in THF (5 ml). 40% sodium hydride (65 mg) was added, and the mixture was stirred for 10 minutes. 2,5-Dichloro-3-trifluoromethylpyridine (350 mg) was added, and the mixture was stirred at room temperature for 12 hours. The mixture was neutralized with 1N-hydrochloric acid and extracted with ethyl acetate. The resulting organic layer was dried over $MgSO_4$, and the solvent was evaporated under reduced pressure. The resulting residue was purified by column chromatography on silica gel to obtain the title compound (398 mg, Yield: 74%).

m.p. 105–106° C.

$^1$H-NMR ($CDCl_3$) δ ppm: 2.94(3H,d,J=5.1 Hz), 3.96 (3H,s), 5.23(2H,s), 6.82(1H,brs), 7.21(1H,dd,J=7.3,1.7 Hz), 7.36(1H,td,J=7.3,1.7 Hz), 7.42(1H,td,J=7.3,1.7 Hz), 7.58(1H,dd,J=7.3,1.7 Hz), 7.81(1H,dd,J=2.4,0.7 Hz), 8.16(1H,dd, J=2.4,0.7 Hz).

The present invention provides an economically and industrially advantageous process for producing a 2-(2-hydroxymethylphenyl)-2-alkoxy(or hydroxy)iminoacetamide derivative which is useful as an intermediate for the production of alkoxyiminoacetamide compounds useful as agricultural fungicides, as well as an intermediate used in the process.

The alkoxyiminoacetamide compound useful as agricultural fungicides can be obtained from the compound (I) in a few steps. Since its E-isomer has more potent fungicidal activity than its Z-isomer, it is preferred to obtain the compound (I) as the E-isomer. In the process of the present invention, the protective group of hydroxyl is removed and isomerization to the E-isomer proceeds at the same time. Therefore this process can provide the E-isomer of the compound (I) in a few steps and in high yield and purity without any separate isomerization step to the E-isomer. This process is thus highly useful for industrial production.

What is claimed is:

1. A compound of the formula (VI'):

(VI')

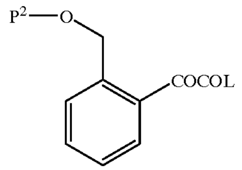

wherein L is a halogen atom or alkoxy, and $P^2$ is aralkyl, trialkylsilyl, triaralkylsilyl, alkyldiarylsilyl, alkoxyalkyl, alkoxyalkoxyalkyl, alkylthioalkyl, tetrahydropyranyl, tetrahydrothiopyranyl, tetrahydrofuranyl, tetrahydrothiofuranyl or aralkyloxyalkyl.

2. The compound according to claim 1, wherein L is alkoxy.

3. A compound according to claim 1, wherein $P^2$ is triphenylmethyl, t-butyldimethylsilyl, triisopropylsilyl, tribenzylsilyl, methoxymethyl, 1-ethoxyethyl, 1-methyl-1-methoxyethyl, tetrahydropyranyl, tetrahydrothiopyranyl, tetrahydrofuranyl or tetrahydrothiofuranyl.

4. A compound according to claim 1, wherein $P^2$ is 1-ethoxyethyl, tetrahydropyranyl or tetrahydrofuranyl.

* * * * *